(12) United States Patent
Ribble et al.

(10) Patent No.: US 11,583,449 B2
(45) Date of Patent: Feb. 21, 2023

(54) SYSTEMS FOR RECOGNIZING TEMPERATURE AS A SIGN OF SURGICAL INFECTION AND METHODS OF USING THE SAME

(71) Applicant: Hill-Rom Services, Inc., Batesville, IN (US)

(72) Inventors: David Lance Ribble, Indianapolis, IN (US); Craig Meyerson, Syracuse, NY (US); Henry J. Smith, Auburn, NY (US); Kirsten Emmons, Batesville, IN (US); Yongji Fu, Harrison, OH (US); David E. Quinn, Auburn, NY (US); Frank E. Sauser, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 931 days.

(21) Appl. No.: 16/432,278

(22) Filed: Jun. 5, 2019

(65) Prior Publication Data

US 2019/0374387 A1   Dec. 12, 2019

Related U.S. Application Data

(60) Provisional application No. 62/681,379, filed on Jun. 6, 2018.

(51) Int. Cl.
*A61F 13/00* (2006.01)
*A61B 5/00* (2006.01)
*A61F 13/02* (2006.01)

(52) U.S. Cl.
CPC ...... *A61F 13/00063* (2013.01); *A61B 5/0008* (2013.01); *A61B 5/6833* (2013.01);
(Continued)

(58) Field of Classification Search
None
See application file for complete search history.

(56) References Cited

U.S. PATENT DOCUMENTS

| 2013/0271278 | A1* | 10/2013 | Duesterhoft | A61B 5/445 340/539.12 |
| 2016/0166438 | A1 | 6/2016 | Rovaniemi | |
| 2020/0289347 | A1* | 9/2020 | Gowans | A61M 1/00 |

OTHER PUBLICATIONS

Zamora, et al, Potentiometric textile-based pH sensor, Sensors and Actuators B: Chemical journal, 2018, pp. 601-608, Elsevier.

(Continued)

*Primary Examiner* — Jay B Shah
(74) *Attorney, Agent, or Firm* — Dinsmore & Shohl LLP

(57) ABSTRACT

A system for detecting potential for infection includes a wound dressing and an electronics component. The wound dressing includes a temperature sensing layer and a cover layer comprising a substrate and a backing layer. The electronics component includes a power source, an electronic control unit (ECU), and a communications interface positioned within a housing and removably coupled to the temperature sensing layer of the wound dressing. The electronics component is configured to receive a plurality of temperature readings from the temperature sensing layer, and provide an indication of potential infection of the wound based the plurality of temperature readings. In various embodiments, each of the plurality of temperature readings corresponds to a temperature of an area around a wound. Methods for preventing infections using the system are also described.

18 Claims, 4 Drawing Sheets

(52) U.S. Cl.
CPC ............ *A61F 13/0209* (2013.01); *A61B 5/44* (2013.01); *A61B 2560/0214* (2013.01); *A61B 2562/0271* (2013.01); *A61F 2013/00953* (2013.01)

(56) References Cited

OTHER PUBLICATIONS

Murata Manufacturing Co., Ltd., NTC Array Sensor—Temperature mapping—, Apr. 27, 2017, 5 pages, Murata Manufacturing Co., Ltd.

* cited by examiner

SYSTEMS FOR RECOGNIZING TEMPERATURE AS A SIGN OF SURGICAL INFECTION AND METHODS OF USING THE SAME

CROSS-REFERENCE TO RELATED APPLICATIONS

The present application claims the benefit of U.S. Provisional Application Ser. No. 62/681,379 filed Jun. 6, 2018 and entitled "Systems For Recognizing Temperature As A Sign Of Surgical Infection And Methods of Using the Same," the entirety of which is incorporated by reference herein.

TECHNICAL FIELD

The present specification generally relates to systems for monitoring surgical sites and, more particularly, to systems for recognizing temperature as a sign of surgical infection.

BACKGROUND

Surgical site infection is a major postoperative complication that can increase the cost of patient care and lead to readmission of the patient. If recognized early, treatment of surgical site infection is typically more effective.

Accordingly, a need exists for systems that monitoring surgical sites and can recognize signs of surgical infection.

SUMMARY

According to some embodiments of the present disclosure, a system for detecting potential for infection includes a wound dressing and an electronics component. The wound dressing includes a temperature sensing layer and a cover layer comprising a substrate and a backing layer. The electronics component includes a power source, an electronic control unit (ECU), and a communications interface positioned within a housing and removably coupled to the temperature sensing layer of the wound dressing. The electronics component is configured to receive a plurality of temperature readings from the temperature sensing layer, and provide an indication of potential infection of the wound based the plurality of temperature readings. In various embodiments, each of the plurality of temperature readings corresponds to a temperature of an area around a wound. Methods for preventing infections using the system are also described.

According to some embodiments of the present disclosure, a method of preventing infection of a wound includes applying to the wound a wound dressing, receiving a plurality of temperature readings at an electronics component, determining a potential for infection of the wound based on the plurality of temperature readings, and altering a treatment plan responsive to determining the potential for infection of the wound. The wound dressing includes a temperature sensing layer removably coupled to the electronics component. The electronics component includes a power source, an electronic control unit (ECU), and a communications interface positioned within a housing. Each of the plurality of temperature readings from the temperature sensing layer corresponds to a temperature of an area around the wound.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

Referring now to the illustrative examples in the drawings, wherein like numerals represent the same or similar elements throughout.

DETAILED DESCRIPTION

Figure 1:
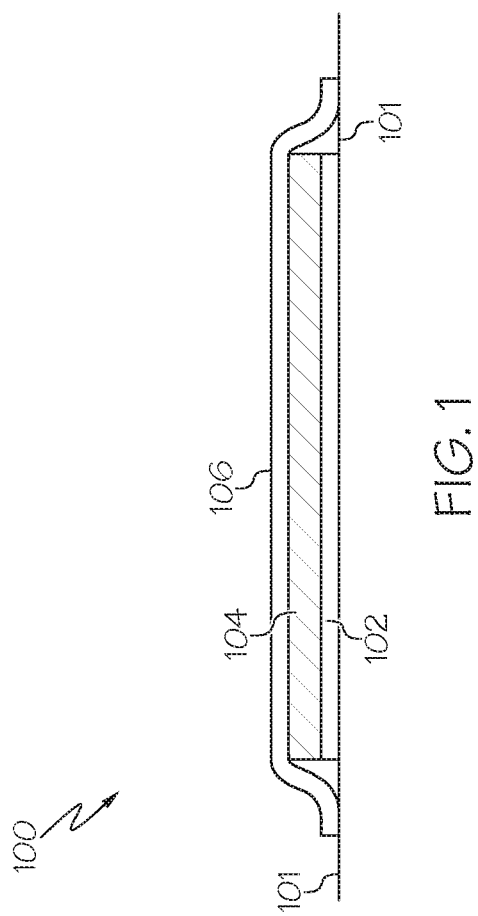
FIG. 1 is a cross-sectional view of a temperature sensing system in the form of a wound dressing according to one or more embodiments shown and described herein.

FIG. 1 generally depicts one embodiment of a system including a wound dressing and an electronics component. The wound dressing includes a temperature sensing layer and a cover layer including a substrate and a backing layer. The electronics component includes a power source, an electronic control unit (ECU), and a communications interface positioned within a housing. The electronics component is removably coupled to the temperature sensing layer of the wound dressing. Accordingly, the electronics component is configured to receive a plurality of temperature readings from the temperature sensing layer, each of which corresponds to a temperature of an area around a wound, and provide an indication of potential infection of the wound based on the plurality of temperature readings. Various embodiments of systems for prediction infection based on temperature and the use thereof will be described in more detail herein.

A wound dressing 100 according to various embodiments is depicted in FIG. 1. As shown in FIG. 1, the wound dressing 100 includes a temperature sensing layer 102 and a cover layer including a substrate 104 and a backing layer 106. In practice, the backing layer 106 is adhered to the skin of an individual around a wound (i.e., the periwound) and remains in place while the temperature sensing layer 102 collects temperature readings which correspond to a temperature of the area 101 around the wound.

Figure 4:
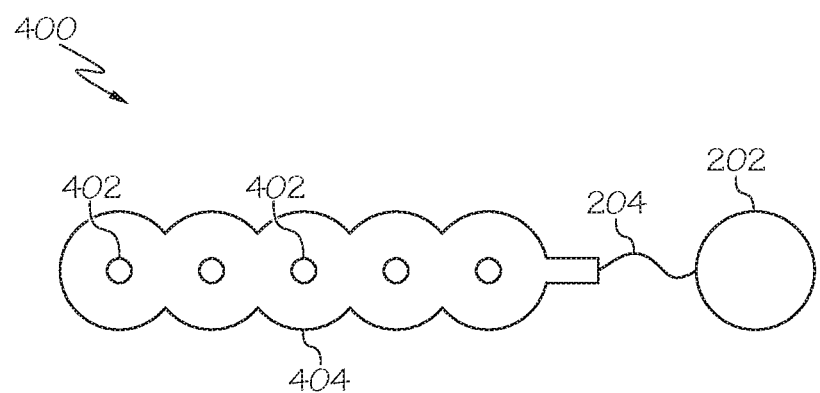
FIG. 4 schematically depicts a temperature sensing strip according to one or more embodiments shown and described herein.

As shown in FIG. 1, the temperature sensing layer 102 and the substrate 104 may have corresponding shapes. Illustratively, the temperature sensing layer 102 and the substrate 104 have a roughly square shape that may be appropriate for use in any desired area of an individual's body. However, in other embodiments, the temperature sensing layer 102 and the substrate 104 may have any appropriate shape, for example, a circular, rectangular, or triangular shape. In still other embodiments, it is contemplated that the temperature sensing layer 102 and the substrate 104 may have shapes that differ from one another. For example, the temperature sensing layer 102 may be in the form of a strip of temperature sensors, as depicted in FIG. 4, while the substrate 104 has a substantially square shape.

In various embodiments, the substrate 104 can be in the form of an absorbent layer and/or a moisturizing layer, for example. The absorbent layer transports wound fluid (exudate) away from the wound and absorbs exudate. In some embodiments, the absorbent layer may allow lateral spread of the exudate to maximize absorbency, while in other embodiments, the absorbent layer may limit lateral spread of the exudate. The reduction in lateral spread afforded by a wound dressing may reduce maceration of skin surrounding the wound.

The moisturizing layer provides the wound with moisturizing or other suitable wound treatment (therapeutic) compounds, including but not limited to, biologics, antibiotics, or the like. Accordingly, in various embodiments, the moisturizing layer is a layer impregnated or saturated with an active agent, such as a moisturizer, biologic, antibiotic, or the like. In one embodiment, the moisturizing layer is a hydrogel, alginate, silver ion, foam, hydrocolloid, or mesalt layer. The moisturizing layer can, in various embodiments, release the active agent from the moisturizing layer to be absorbed by the wound. In such embodiments, the cover layer can be replaced when the moisturizing layer has released a substantial portion of the active agent. However, in other embodiments, the active agent can be maintained within the moisturizing layer at a location proximate to the wound.

In embodiments, the substrate 104 is fibrous and, for example, includes gel forming fibers. In various embodiments, the substrate 104 is non-woven. Without being bound by theory, it is believed that fibrous layers are advantageous because they are able to gel block which resists the lateral spread of exudate. In addition, exudate is absorbed rapidly and retained under pressure. Fibers suitable for use include, by way of example and not limitation, hydrophilic fibers which upon the uptake of wound exudate become moist and slippery or gelatinous and thus reduce the tendency for the surrounding fibers to adhere to the wound. In some embodiments, the fibers can be of the type which retain their structural integrity on absorption of exudate, or they can be of the type which lose their fibrous form and become a structure-less gel or a solution on absorption of exudate. Gel forming fibers can be, for example, chemically-modified cellulosic fibers, such as carboxymethylated cellulose fibers.

The substrate 104 may, in addition to or as an alternative to the gel forming fibers, also comprise other fibers such as textile fibers which can be natural or synthetic such as cellulosic fibers, for example, viscose rayon, multi-limbed viscose, cotton, or regenerated cellulose or fibers having a higher absorbency than most textiles. Without being bound by theory, the use of a blend of gel forming and cellulosic fibers may reduce shrinkage of the dressing. In particular, the inclusion of the cellulosic fibers may help maintain the shape and structure of the substrate 104 while in use.

In still other embodiments, the substrate 104 can be an absorbent polymeric substrate, a foam, an alginate, or a hydrocolloid. Absorbent polymeric materials may include, by way of example and not limitation, modified starch, polymerized polyvinyl alcohol, polyethylene oxide, and polyacrylates. Foams suitable for use include flexible, open-cell foams that are at least slightly hydrophilic. Without being bound by theory, the open cells permit transport of fluid and cellular debris into and through the foam. Various cell sizes are contemplated, provided that they are large enough to promote fluid transport through the layer. Suitable foams can include foams made from polyurethane, cellulose, carboxylated butadiene-styrene rubber, polyester foams, hydrophilic epoxy foams or polyacrylate foams.

Suitable hydrocolloids include, but are not limited to, natural gums such as arabic gum, ghatti gum, karaya gum, tragacanth gum, guar gum, locust bean gum and acacia gum; seaweed extracts such as agar, algin, alginate salts and carrageenan; cereal gums; starches; fermentation or microbial gums such as dextran gum and xanthan gum; pectins; gelatins; casein; and collagens. Modified forms of the hydrocolloids may also be used, including, for example, the oxidized, acetylated, carboxylated, esterified, methylated, aminated, etherated, sulfated, borated and phosphated derivatives of the hydrocolloid absorptive agents. Suitable synthetic gums include polyvinylpyrrolidone, low methoxyl pectin, propyleneglycol alginates, carboxymethyl locust bean gum and carboxymethyl guar gum.

Other materials are contemplated for use as the substrate 104, provided they are suitable for medical use. Additionally, it is contemplated that the particular material forming the substrate 104 can be selected based on the status of the wound to which the wound dressing is to be applied. For example, a substrate 104 formed from a superabsorbent material, calcium alginate, and/or collagen can be utilized when the wound has heavy drainage, while a substrate 104 formed from a hydrogel gauze or hydrogel sheet can be utilized when the wound is a dry wound with minimal wound drainage.

In various embodiments, the substrate 104 can be in the form of a sheet, although it is contemplated that in some embodiments, the substrate 104 can include patterning or other structural features to enhance the absorbency of the substrate 104. For example, channels or receptacles can be formed in the substrate 104 to direct the exudate away from the periwound and redistribute the exudate through the substrate 104.

The backing layer 106 may be of any suitable material known for use in the preparation of wound dressings (e.g. a foam, a non-woven layer or a polyurethane, polyethylene, polyester or polyamide film). In various embodiments, the backing layer 106 is water impermeable and vapor permeable, such as a layer made from a coated woven or non-woven nylon or polyester, a polyurethane film, or the like. In embodiments in which the backing layer 106 is a coated layer, the coating may be, for example, a thermoplastic polyurethane. Without being bound by theory, the use of a water impermeable, vapor permeable material as the backing layer 106 enables the dressing to be worn while the individual bathes or showers without the wound becoming wet. In various embodiments, the backing layer 106 provides a barrier to bacteria (including MRSA), viruses, and other external contaminants, sealing the wound area from external pathogens.

In various embodiments, the wound dressing 100 may be made from materials that render the wound dressing 100 suitable for use in negative pressure wound therapy (NWPT). Typically in NPWT the wound cavity or surface is filled or covered with a material that allows the transmission of a partial vacuum (i.e., does not completely collapse) to the wound bed when a negative pressure is applied to the wound area, and also allows fluids to pass from the wound bed towards the source of negative pressure. There are two primary approaches to NPWT, gauze or foam types. The gauze type (also referred to as the Chariker-Jeter technique) involves the use of a drain wrapped in gauze topped by a sealed dressing. The foam type involves the use of foam placed over or in the wound. Accordingly, in various embodiments, the wound dressing 100 can include gauze or foam, such as in the form of the substrate 104.

In embodiments in which the wound dressing 100 is suitable for use in NWPT, it is contemplated that the wound dressing 100 may include one or more apertures suitable for a tube connected to a vacuum source to be inserted through. Accordingly, when the wound dressing 100 is in place, fluid may be transmitted through the tube to a collection receptacle positioned between the end of the tube and the vacuum source.

In some embodiments, the wound dressing 100 may also include a facing layer (not shown) positioned between the temperature sensing layer 102 and the wound area 101. The facing layer can be formed from a material selected from the group consisting of a non-woven fabric (e.g., containing polyethylene (PE), polyethylene terephthalate (PET), polypropylene (PP), polyamide or polytetrafluoroethylene (PTFE)), a perforated sheet (e.g., containing polyethylene (PE), polyethylene terephthalate (PET), polypropylene (PP), polyamide or polytetrafluoroethylene (PTFE)), a perforated sheet laminated on a non-woven fabric (e.g., containing polyethylene (PE), polyethylene terephthalate (PET), polypropylene (PP), polyamide or polytetrafluoroethylene (PTFE)) a fine net or screen (e.g., containing polyethylene (PE), polyethylene terephthalate (PET), polypropylene (PP), polyamide or polytetrafluoroethylene (PTFE)), a perforated foam or sheet comprising polyurethane, a perforated material based on silicone or a foam with open cells based on polyurethane or silicone or a combination thereof. In embodiments in which a facing layer is included as part of the wound dressing 100, the facing layer may reduce sticking between the temperature sensing layer 102 and the wound area 101. Accordingly, in some embodiments, the facing layer may be coated with a non-sticking material, such as silicone.

In various embodiments, the wound dressing 100 can additionally include one or more additional therapeutic layers. The therapeutic layer may include, by way of example and not limitation, moisture-retentive foam, film, hydrogel, hydrocolloid, alginates, biologics, skin substitutes, and combinations thereof. In some embodiments, the wound dressing 100 may include components forming a negative pressure wound therapy (NPWT) system. The wound dressing 100 may also include, an odor-absorbing layer, such as an activated carbon layer, or the like, in some embodiments. Although it is contemplated that a therapeutic layer can be included as a distinct layer within the wound dressing 100, in some embodiments, therapeutic agents, including moisture-retentive foams, films, hydrogels, hydrocolloids, alginates, biologics, and/or skin substitutes can be incorporated into other layers of the wound dressing, such as the substrate 104.

The layers of the wound dressing 100, including at least the substrate 104 and the backing layer 106, can be connected together using any suitable method. For example, the backing layer 106 may be adhered to the substrate 104 using an adhesive, heat sealed, crimped, stitched, or embossed. However, other methods for joining the layers together are contemplated. In some embodiments, the temperature sensing layer 102 may be connected to the substrate 104 and the backing layer 106, although it is contemplated that in other embodiments, the temperature sensing layer 102 may be applied as a separate layer, independent of the wound dressing 100.

Figure 2A:
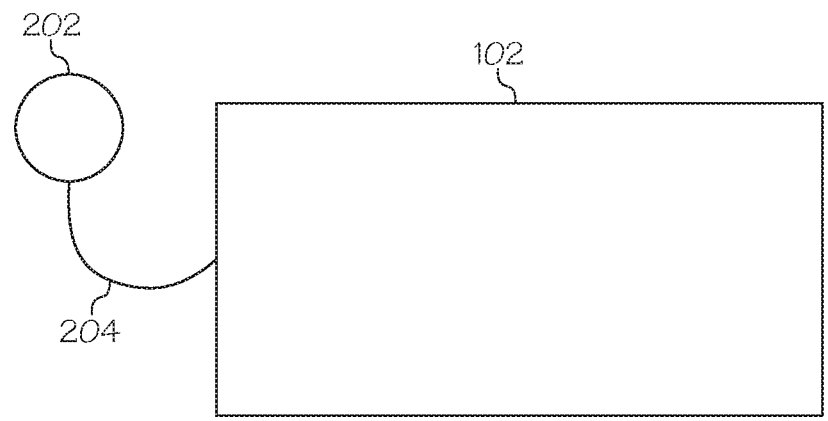
FIG. 2A schematically depicts a temperature sensing system having reusable electronics according to one or more embodiments shown and described herein.

FIG. 2A schematically depicts the temperature sensing layer 102 in greater detail. In particular, the temperature sensing layer 102 is removably coupled to an electronics component 202 via a wire 204. Although depicted in FIG. 2A as being rectangular in shape, it is contemplated that the temperature sensing layer 102 can have any one of a number of shapes, including square, rectangular, or an irregular shape, as discussed above. The temperature sensing layer 102 generally includes a plurality of temperature sensors disposed throughout the temperature sensing layer 102. Each of temperature sensors may be, for example, a thermistor, an infrared temperature sensor, a thermocouple, a semi-conductor based temperature sensor, or any other type of temperature sensor known to those in the art and suitable for use in detecting the temperature of an area of skin. For example, in some embodiments, the temperature sensing layer 102 may include a plurality temperature sensors that output a signal (i.e., a temperature signal or temperature reading) indicative of the temperature of an object on which it is positioned joined together via a flexible substrate. In various embodiments, the temperature sensors may be embedded in the flexible substrate and communicatively coupled to the electronics component 202, such as with wire 204.

In various embodiments, the temperature sensors are positioned to detect the temperature of the skin in an area 101 around a wound over which the wound dressing 100 is placed. Each of the plurality of temperature sensors may detect the temperature from one of a corresponding plurality of locations with respect to the wound. In various embodiments, each of the plurality of temperature readings is obtained within about 1.5 cm from an edge of the wound, or within about 1.25 cm from an edge of the wound. In embodiments, the temperature readings provided by the plurality of temperature sensors to the electronics component 202 may be used, for example and without limitation, to determine a potential for infection of the wound and/or to determine whether a treatment plan should be altered.

Figure 2B:
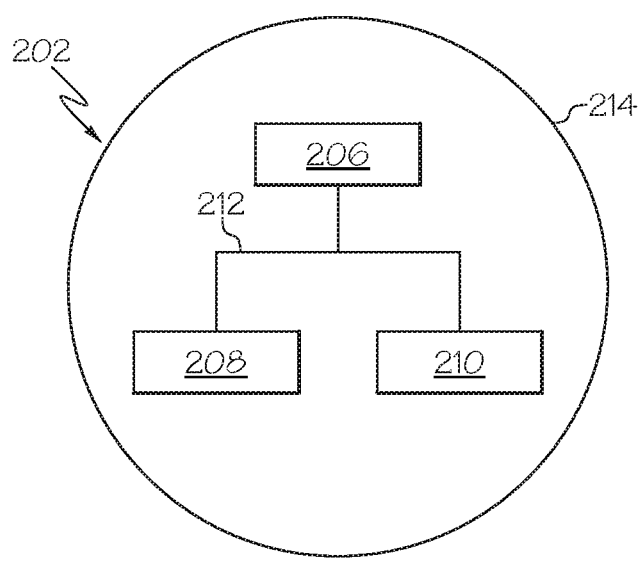
FIG. 2B schematically depicts the reusable electronics of FIG. 2A in greater detail according to one or more embodiments shown and described herein.

As shown in FIG. 2B, the electronics component 202 includes a power source 206, an electronic control unit (ECU) 208, and a communications interface 210 connected to one another through a bus 212. The power source 206 supplies power to at least the ECU 208 and the related components, including the temperature sensing layer 102 when electrically connected thereto via the wire 204. In various embodiments, the power source 206 is a DC power source, such as a battery.

The ECU 208 may include a processor for executing machine readable and executable instructions and a non-transitory electronic memory for storing the machine readable and executable instructions. In embodiments, the processor may be an integrated circuit, microchip, computer, or any other computing device capable of executing machine readable and executable instructions. The electronic memory may be RAM, ROM, flash memory, a hard drive, or any other form of non-transitory memory capable of storing machine readable and executable instructions. In the embodiments described herein, the processor and the electronic memory are integral with the ECU 208. However, it is noted that, in alternative embodiments, the ECU 208, the processor, and the electronic memory may include a series of discrete components in electrical communication with one another. The machine readable and executable instructions stored in the electronic memory of the ECU 208 facilitate the operation of the temperature sensing layer 102 including, without limitation, the collection of data (i.e., temperature readings) and the transmission of that data to a receiving unit (e.g., receiving unit 304 in FIG. 3).

In embodiments, the ECU 208 may be configured to receive temperature readings in the form of electrical signals from the temperature sensing layer 102 via the wire 204. In embodiments, the ECU 208 may be configured to determine a potential for infection of the wound based on the temperature readings received from the temperature sensing layer 102 and provide an indication of potential infection of the wound to the receiving unit 304 via the communications interface 210.

In various embodiments, the communications interface 210 enables communications between the electronics component 202 and one or more additional computing devices, such as receiving unit 304. In embodiments, the communications interface 210 communicatively couples the electronics component 202 to the one or more additional computing devices wirelessly, such as through Bluetooth® communication protocols, IEEE 802.11 wireless communication protocols, near-field communication protocols, or any other communication protocol suitable for facilitating radio frequency communications between electronic devices. Alternatively, the electronics component 202 may be directly coupled to the one or more additional computing devices, such as by wires and/or optical fiber.

In the embodiments described herein, the bus 212 may be formed from any medium that is suitable for transmitting data in the form of electrical and/or optical signals such as, for example, conductive wires, conductive traces, optical waveguides, or the like. In some embodiments, the power source 206, the ECU 208, and the communications interface 210 are positioned on an electronic substrate, such as a silicon wafer or the like, and the bus 212 is a series of electrical traces interconnecting the various components of the electronics component 202.

The power source 206, ECU 208, communications interface 210, and bus 212 are positioned within a housing 214, which encapsulates the electronics component 202. As with the other components of the system, the housing 214 can have any suitable size and shape. Additionally, in various embodiments, the electronics component 202 can include additional components which can impart additional functionality to the system. In various embodiments described herein, the electronics component 202 is removably connected to the temperature sensing layer 102 such that the temperature sensing layer 102 may be disposed of while the electronics component 202 may be coupled to a new temperature sensing layer 102. For example, the temperature sensing layer 102 may be replaced after a period of time, and/or can be changed between users, while the electronics component 202 may be re-used. For example, the electronics component 202 may be decoupled from the temperature sensing layer 102, and the wound dressing 100 including the temperature sensing layer 102 may be removed from the wound. For example, the wound dressing 100 may be removed to examine the wound or to replace the wound dressing. Thus, a subsequent wound dressing including a subsequent temperature sensing layer may be applied to the wound and the electronics component 202 may be coupled to the subsequent temperature sensing layer.

Figure 3:
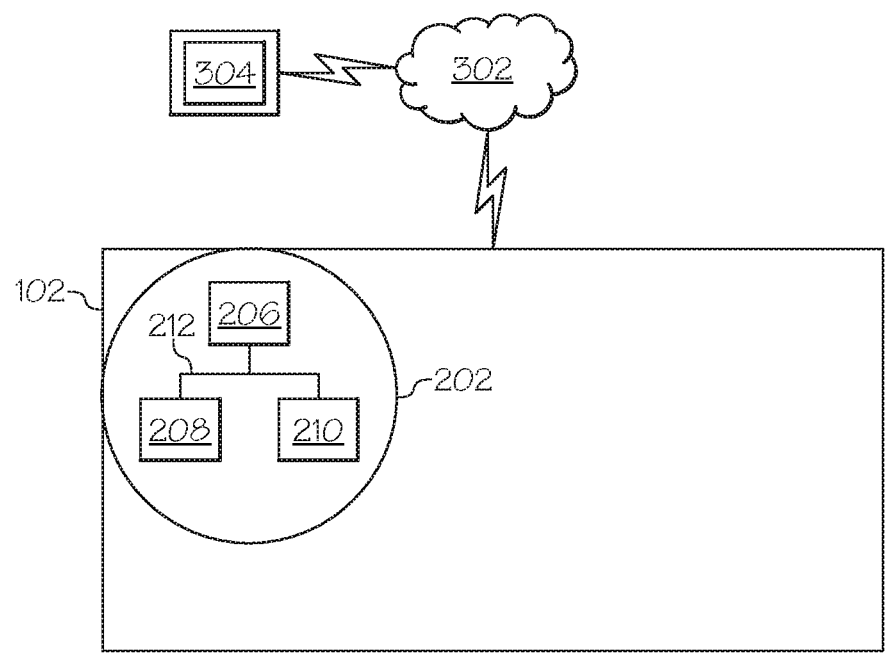
FIG. 3 schematically depicts a temperature sensing system having incorporated electronics according to one or more embodiments shown and described herein.

Alternatively, it is contemplated that in some embodiments, the electronics component 202 may be integrated with the temperature sensing layer 102, such as in the embodiment depicted in FIG. 3. In FIG. 3, instead of being a standalone component that is removably coupled to the temperature sensing layer 102, the electronics component 202 is disposed directly on the temperature sensing layer 102. In such embodiments, the power source 206, the ECU 208, the communications interface 210, and the bus 212 may or may not be contained within a housing.

Regardless of whether the electronics component 202 is removably coupled to the temperature sensing layer 102 or integrated with the temperature sensing layer 102, in various embodiments, the electronics component 202 communicates with the receiving unit 304 via a network 302. The network 302 may be, for example, the internet, an intranet, or any other type of wireless communications network that enables communication between the electronics component 202 and the receiving unit 304.

The receiving unit 304 is not particularly limited, and can be any type of computing device configured to receive information from the electronics component 202. In some embodiments, the receiving unit 304 may be further configured to transmit information to the electronics component 202. In some embodiments, the receiving unit 304 includes a receiver, an electronic control unit, and a power source, which may be coupled to one another via a bus, as described in detail above with regards to the electronics component 202. The receiving unit 304 may be, for example, a smartphone, tablet computer, or other computing device. In some embodiments, the receiving unit 304 is configured to receive the indication of potential infection of the wound from the electronics component 202 and provide instructions to a caregiver to alter a treatment plan in response to the indication of potential infection, such as by displaying a new treatment plan on a display integrated with or otherwise coupled to the receiving unit 304. In other embodiments, the receiving device may be configured to receive the plurality of temperature readings from the electronics component 202 and determine the potential for infection of the wound based on the plurality of temperature readings. In other words, the determination of the potential for infection may be determined by the electronics component 202 or by the receiving unit 304, depending on the particular embodiment, as will be discussed in greater detail below.

Although in various embodiments the temperature sensing layer 102 has been described as including a two-dimensional matrix of temperature sensors, it is contemplated that in other embodiments, the temperature sensing layer 102 can include temperature sensors 402 arranged in a temperature sensing strip 400 along a single dimension, as shown in FIG. 4. The temperature sensing strip 400 can include a plurality of temperature sensors 402 coupled via a substrate 404 that may be of any size and shape. As with the temperature sensing layer 102 in the form of a two-dimensional matrix, the temperature sensing strip 400 may be coupled to the electronics component 202 via a wire 204 at one end of the temperature sensing strip 400.

Other embodiments for the temperature sensing layer 102 are further contemplated. For example, in some embodiments, commercially available temperature sensing technologies may be employed. By way of example and not limitation, commercially available temperature patches, flexible circuits including silver ink on thin plastic substrates, and screened thermistors may be used.

In embodiments, the temperature sensing layer 102 may further include one or more sensors (not depicted) for detecting the pH of the wound. An example of a suitable sensor includes, without limitation, the pH sensors disclosed in "Potentiometric textile-based pH sensor", Sensors and Actuators B: Chemical, Volume 260, 1 May 2018, pp. 601-608. However, it should be understood that other pH sensors are contemplated and possible. The pH sensor may be coupled to the electronics component 202 in a similar manner as described herein with respect to the temperature sensing layer 102. The pH sensor may be positioned in the temperature sensing layer 102 to facilitate detection of the pH of secretions from the wound and the electronics component 202 may be configured to determine changes in the pH of secretions from the wound based on the detected pH. Changes in the pH of the secretions from the wound may provide an indication of a change in the status of the wound, such as, for example, the development of an infection in the wound. In embodiments, the change in the pH of secretions from the wound may be used in conjunction with temperature readings from the skin around the wound to determine the onset of infection. In embodiments, the change in the pH of secretions from the wound may be used apart from the temperature readings from the skin around the wound to determine the onset of infection.

When the wound dressing 100 is in use, the wound dressing 100 is adhered to the skin of an individual by placing the temperature sensing layer 102 into contact with the skin. In various embodiments, the wound dressing 100 is positioned such that the temperature sensing layer 102 extends over the wound area and no adhesive (such as may be present on the backing layer 106 to adhere the wound dressing 100 to the skin) is in contact with the wound area. In embodiments, a backing strip or other removable layer may be removed from the wound dressing 100 in order to expose an adhesive on the backing layer 106 for contacting it with the skin.

When in place, the temperature sensing layer 102 can detect the temperature of the area around the wound and transmit a plurality of temperature readings to the electronics component 202. The electronics component 202 receives the plurality of temperature readings and determines a potential for infection of the wound based on the plurality of temperature readings. The potential for infection of the wound may be determined according to any one or more of a variety of methods, as will be described in greater detail.

In one example method, a potential for infection is determined using a temperature differential. For example, in embodiments, a baseline temperature $T_0$ may be obtained when the wound dressing 100 is placed. The baseline temperature $T_0$ may be stored by the ECU 208 for each individual temperature sensor. Alternatively, in some embodiments, the baseline temperature $T_0$ may be calculated as an average of the plurality of temperature readings received when the wound dressing 100 is placed. In various embodiments employing the temperature differential method, the system may determine a potential for infection responsive to one of the plurality of temperature readings being below the baseline temperature $T_0$ by at least about 0.75° C., by at least about 1.0° C., or even by at least about 2.0° C. For example, the system may calculate an average temperature of the skin around the wound of about 40° C. when the wound dressing 100 is placed over the wound following a surgery. The average temperature can be calculated using temperature readings from each of the plurality of temperature sensors in the temperature sensing layer 102, or a subset thereof. For example, in some embodiments, a local average for a "zone" of temperature sensors can be calculated, and each temperature reading from the temperature sensors within a zone can be compared to the local average. The temperature sensing layer 102 can detect the temperature of the area around the wound over time, and when one or more of the temperature readings is about 39.25° C. or less (i.e., below the baseline temperature $T_0$ by at least about 0.75° C.), the system may determine the potential for infection. As another example, the system may determine that an initial temperature of the skin at the position of one temperature sensor is about 40° C. when the wound dressing 100 is placed over the wound following a surgery. The temperature sensing layer 102 can detect the temperature of the area around the wound over time, and when a subsequent temperature reading from that temperature sensor is about 39.25° C. or less (i.e., below the baseline temperature $T_0$ by at least about 0.75° C.), the system may determine the potential for infection.

In a similar method, a potential for infection is determined using a temperature differential between the temperature of the skin in the area around the wound and an area further away from the wound. For example, in embodiments, a baseline temperature $T_0$ may be obtained when the wound dressing 100 is placed using a plurality of temperature sensors that are greater than about 1.25 cm away from the edge of the wound and calculating an average of the plurality of temperature readings received. In various embodiments, the system may determine a potential for infection responsive to one of the plurality of temperature readings obtained within about 1.25 cm from an edge of the wound being below the baseline temperature $T_0$ by at least about 0.75° C., by at least about 1.0° C., or even by at least about 2.0° C. For example, the system may calculate an average temperature of the skin greater than about 1.25 cm away from the edge of the wound of about 40° C. when the wound dressing 100 is placed over the wound following a surgery. The temperature sensing layer 102 can detect the temperature of the area around the wound over time, and when one or more of the temperature readings within about 1.25 cm of the edge of the wound is about 39.25° C. or less (i.e., below the baseline temperature $T_0$ by at least about 0.75° C.), the system may determine the potential for infection.

In another example method, a potential for infection is determined using a threshold temperature. For example, in embodiments, a threshold temperature $T_T$ may be set when the wound dressing 100 is placed. The threshold temperature $T_T$ may be stored by the ECU 208, and may be selected based on clinical recommendations, patient history, or other factors. Alternatively, in some embodiments, the threshold temperature $T_T$ may be calculated as an average of the plurality of temperature readings received when the wound dressing 100 is placed. In various embodiments employing the threshold temperature method, the system may determine a potential for infection responsive to one of the plurality of temperature readings being below the threshold temperature $T_T$. For example, the threshold temperature $T_T$ may be set to about 33.0° C. or lower. The temperature sensing layer 102 can detect the temperature of the area around the wound over time, and when one or more of the temperature readings is from about 30.5° C. to about 33.0° C. (i.e., below the threshold temperature $T_T$), the system may determine the potential for infection.

In various embodiments, determining the potential for infection of the wound takes into account the time at which the temperature readings are obtained following surgery. In particular, in various embodiments, determining the potential for infection of the wound is based on a decrease in temperature within a time of from about 24 hours to about 72 hours following surgery. For example, the temperature readings may be obtained for a time period following surgery until about 24 hours after surgery, about 36 hours after surgery, about 48 hours after surgery, or about 72 hours after surgery. Without being bound by theory, it is believed that skin in the area around a wound may be lower in subjects that develop a surgical site infection in the 24 to 72 hours following surgery. Accordingly, in various embodiments, each of the plurality of temperature readings is received within about 72 hours after surgery, within about 48 hours after surgery, or even within about 36 hours after surgery. It is contemplated that in some embodiments, the threshold temperature and/or the acceptable temperature differential may vary depending on the time of the temperature readings with respect to surgery.

Figure 5:
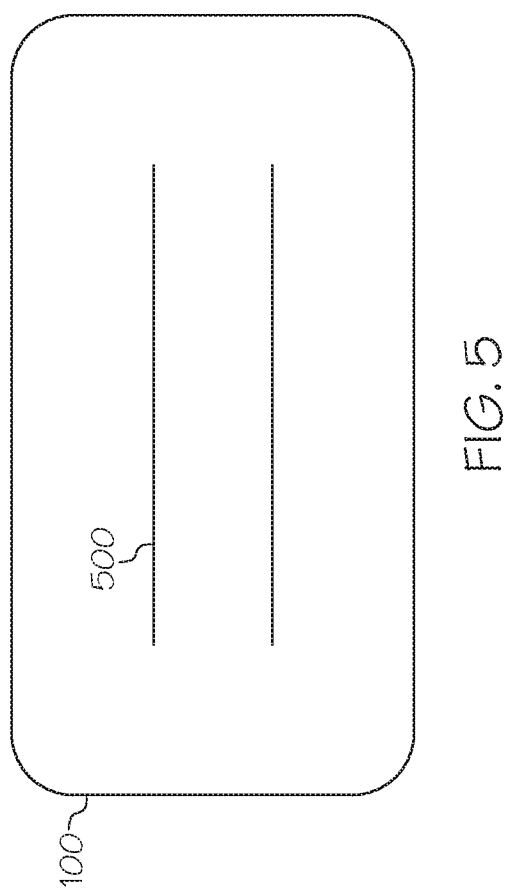
FIG. 5 schematically depicts a temperature sensing system having indicia thereon according to one or more embodiments shown and described herein.

Additionally or alternatively, in various embodiments, determining the potential for infection of the wound takes into account the location at which the temperature readings are obtained with respect to the wound. For example, as described above, in some embodiments, temperature readings are obtained within about 1.5 cm or within about 1.25 cm of an edge of the wound. Accordingly, in some embodiments, the wound dressing 100 may include one or more indicia 500 to assist with proper placement of the wound dressing 100, as shown in FIG. 5. For example, the wound dressing 100 may include indicia 500 on the backing layer 106 to indicate to a caregiver that the wound should be located between the indicia 500. The indicia 500 may be printed on or woven into the backing layer 106, for example. In embodiments, the location of the temperature sensor with respect to the wound may be factored into the determination of the potential for infection. For example, an algorithm executed by the ECU can produce a weighted temperature value based on the location of the temperature sensor, and/or can select a threshold temperature and/or local average based on the location of the temperature sensor.

After determining that there is the potential for infection of the wound, in various embodiments, the system provides an indication of the potential infection of the wound. For example, the system may provide an alert to the receiving unit 304. The alert can be, for example, an auditory, haptic, or visual alert. Visual alerts may range from a flashing LED light to a detailed alert providing information to a caregiver that the subject is at risk for infection. In various embodiments, the treatment plan in place for the wound is altered responsive to determining the potential for infection. In one example, the system can provide an updated treatment plan to the caregiver via the receiving unit 304. The updated treatment plan can include instructions to administer medications to prevent the infection, instructions to change the dressing more frequently, or the like.

While the foregoing method relates to the use of temperature measurements to determine the potential for infection in the wound, it should be understood that other methods are contemplated and possible. For example, a pH sensor integrated into the temperature sensing layer, as described herein, may be used to identify changes in the pH of secretions from the wound and, when a determination is made that the pH of the wound has changed, the system may provide an alert to the receiving unit 304. The alert can be, for example, an auditory, haptic, or visual alert. Visual alerts may range from a flashing LED light to a detailed alert providing information to a caregiver that the subject is at risk for infection. In various embodiments, the treatment plan in place for the wound is altered responsive to determining the potential for infection. In one example, the system can provide an updated treatment plan to the caregiver via the receiving unit 304. The updated treatment plan can include instructions to administer medications to prevent the infection, instructions to change the dressing more frequently, or the like. As noted herein, changes in the pH of the wound may be used in conjunction with or separate from changes in the temperature of the wound to determine the potential for infection in the wound.

Many additional embodiments other than those described above are possible and still included in the spirit and scope of the claims defining the embodiments described herein. For example, although various combinations of features of a wound dressing have been shown and described, it is contemplated that these features may be combined in other ways described in detail or illustrated in the accompanying figures.

Embodiments can be described with reference to the following clauses, with preferred features laid out in the dependent clauses.

In a first clause, the disclosure provides a system including a wound dressing and an electronics component. The wound dressing includes a temperature sensing layer and a cover layer comprising a substrate and a backing layer. The electronics component includes a power source, an electronic control unit (ECU), and a communications interface positioned within a housing and removably coupled to the temperature sensing layer of the wound dressing. The electronics component is configured to: receive a plurality of temperature readings from the temperature sensing layer, each of the plurality of temperature readings corresponds to a temperature of an area around a wound; and provide an indication of potential infection of the wound based the plurality of temperature readings.

In a second clause, the disclosure provides the system of the first clause, wherein the plurality of temperature readings are received from a plurality of locations with respect to the wound.

In a third clause, the disclosure provides the system of the first or second clauses, wherein each of the plurality of temperature readings is obtained within about 1.5 cm from an edge of the wound.

In a fourth clause, the disclosure provides the system of any of the preceding clauses, wherein each of the plurality of temperature readings is obtained within about 1.25 cm from an edge of the wound.

In a fifth clause, the disclosure provides the system of any of the preceding clauses, comprising providing the indication of potential infection responsive to one of the plurality of temperature readings being below a temperature reading at a position greater than 1.25 cm from the edge of the wound by at least about 0.75° C.

In a sixth clause, the disclosure provides the system of any of the preceding clauses, wherein a first temperature reading of the plurality of temperature readings is received at a first time and when a second temperature reading of the plurality of temperature readings is received at a second time that is different from the first time.

In a seventh clause, the disclosure provides the system of any of the preceding clauses, comprising providing the indication of potential infection responsive to one of the plurality of temperature readings being below an average of least some of the plurality of temperature readings by at least about 0.75° C.

In an eighth clause, the disclosure provides the system of any of the preceding clauses, comprising providing the indication of potential infection responsive to one of the plurality of temperature readings being below an average of least some of the plurality of temperature readings by at least about 1° C.

In a ninth clause, the disclosure provides the system of any of the preceding clauses, comprising providing the indication of potential infection responsive to one of the plurality of temperature readings being from about 30.5° C. to about 33.0° C.

In a tenth clause, the disclosure provides the system of any of the preceding clauses, wherein each of the plurality of temperature readings is received within about 48 hours after surgery.

In an eleventh clause, the disclosure provides the system of any of the preceding clauses further comprising a pH sensor for detecting a pH of secretions from the wound, wherein the pH sensor is coupled to the electronics component and the electronics component is configured to: determine a change in the pH of the wound; and provide an indication of potential infection of the wound based on the change in the pH of the wound.

According to an twelfth clause, the disclosure provides a method of preventing infection of a wound including applying to the wound a wound dressing comprising a temperature sensing layer removably coupled to an electronics component comprising a power source, an electronic control unit (ECU), and a communications interface positioned within a housing. The method further includes receiving, at the electronics component, a plurality of temperature readings from the temperature sensing layer, each of the plurality of temperature readings from the temperature sensing layer corresponding to a temperature of an area around the wound. Additionally, the method includes determining a potential for infection of the wound based on the plurality of temperature readings, and altering a treatment plan responsive to determining the potential for infection of the wound.

According to a thirteenth clause, the disclosure provides the method of the twelfth clause, wherein determining the potential for infection of the wound based on the plurality of temperature readings comprises determining the potential for infection responsive to one of the plurality of temperature readings being below an average of least some of the plurality of temperature readings by at least about 0.75° C.

According to a fourteenth clause, the disclosure provides the method of the twelfth or thirteenth clauses, wherein determining the potential for infection of the wound based on the plurality of temperature readings comprises determining the potential for infection responsive to one of the plurality of temperature readings being below an average of least some of the plurality of temperature readings by at least about 1° C.

According to a fifteenth clause, the disclosure provides the method any of the twelfth through fourteenth clauses, wherein determining the potential for infection of the wound based on the plurality of temperature readings comprises determining the potential for infection responsive to one of the plurality of temperature readings being from about 30.5° C. to about 33.0° C.

According to a sixteenth clause, the disclosure provides the method any of the twelfth through fifteenth clauses, wherein the plurality of temperature readings is received from a plurality of locations with respect to the wound.

According to a seventeenth clause, the disclosure provides the method any of the twelfth through sixteenth clauses, wherein each of the plurality of temperature readings is obtained within about 1.25 cm from an edge of the wound.

According to a eighteenth clause, the disclosure provides the method any of the twelfth through seventeenth clauses, wherein each of the plurality of temperature readings is received within about 48 hours after surgery.

According to an nineteenth clause, the disclosure provides the method any of the twelfth through eighteenth clauses, further including transmitting an alert regarding the potential for infection to a mobile computing device using the communications interface of the electronics component.

According to a twentieth clause, the disclosure provides the method any of the twelfth through nineteenth clauses, further including: decoupling the electronics component from the temperature sensing layer; removing the wound dressing comprising the temperature sensing layer from the wound; applying a subsequent wound dressing to the wound, the subsequent wound dressing comprising a subsequent temperature sensing layer; and coupling the electronics component to the subsequent temperature sensing layer.

According to a twenty-first clause, the disclosure provides a temperature sensing apparatus according to any of the previous clauses.

According to a twenty-second clause, the disclosure provides a method for predicting infection based on temperature around a wound according to any of the previous clauses.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A system comprising:
   a wound dressing comprising:
      a temperature sensing layer; and
      a cover layer comprising a substrate and a backing layer; and
   an electronics component comprising a power source, an electronic control unit (ECU), and a communications interface positioned within a housing and removably coupled to the temperature sensing layer of the wound dressing, wherein the electronics component is configured to:
      receive a plurality of temperature readings from the temperature sensing layer, each of the plurality of temperature readings corresponding to a temperature of an area around a wound; and
      provide an indication of potential infection of the wound based the plurality of temperature readings, wherein the indication of potential infection is provided responsive to one of the plurality of temperature readings being below an average of at least two of the plurality of temperature readings by at least about 0.75° C.

2. The system of claim 1, wherein the plurality of temperature readings are received from a plurality of locations with respect to the wound.

3. The system of claim 1, wherein each of the plurality of temperature readings is obtained within about 1.5 cm from an edge of the wound.

4. The system of claim 1, wherein each of the plurality of temperature readings is obtained within about 1.25 cm from an edge of the wound.

5. The system of claim 4, comprising providing the indication of potential infection responsive to one of the plurality of temperature readings being below a temperature reading at a position greater than 1.25 cm from the edge of the wound by at least about 0.75° C.

6. The system of claim 1, wherein a first temperature reading of the plurality of temperature readings is received at a first time and when a second temperature reading of the plurality of temperature readings is received at a second time that is different from the first time.

7. The system of claim 1, comprising providing the indication of potential infection responsive to one of the plurality of temperature readings being below an average of at least some of the plurality of temperature readings by at least about 1° C.

8. The system of claim 1, comprising providing the indication of potential infection responsive to one of the plurality of temperature readings being from about 30.5° C. to about 33.0° C.

9. The system of claim 1, wherein each of the plurality of temperature readings is received within about 48 hours after surgery.

10. The system of claim 1, further comprising a pH sensor for detecting a pH of secretions from the wound, wherein the pH sensor is coupled to the electronics component and the electronics component is configured to:
determine a change in the pH of the wound; and
provide an indication of potential infection of the wound based on the change in the pH of the wound.

11. A method of preventing infection of a wound comprising:
applying to the wound a wound dressing comprising a temperature sensing layer removably coupled to an electronics component comprising a power source, an electronic control unit (ECU), and a communications interface positioned within a housing;
receiving, at the electronics component, a plurality of temperature readings from the temperature sensing layer, each of the plurality of temperature readings from the temperature sensing layer corresponding to a temperature of an area around the wound;
determining a potential for infection of the wound based on the plurality of temperature readings, wherein determining the potential for infection of the wound based on the plurality of temperature readings comprises determining the potential for infection responsive to one of the plurality of temperature readings being below an average of at least two of the plurality of temperature readings by at least about 0.75° C.; and
altering a treatment plan responsive to determining the potential for infection of the wound.

12. The method of claim 11, wherein determining the potential for infection of the wound based on the plurality of temperature readings comprises determining the potential for infection responsive to one of the plurality of temperature readings being below an average of at least some of the plurality of temperature readings by at least about 1° C.

13. The method of claim 11, wherein determining the potential for infection of the wound based on the plurality of temperature readings comprises determining the potential for infection responsive to one of the plurality of temperature readings being from about 30.5° C. to about 33.0° C.

14. The method of claim 11, wherein the plurality of temperature readings is received from a plurality of locations with respect to the wound.

15. The method of claim 11, wherein each of the plurality of temperature readings is obtained within about 1.25 cm from an edge of the wound.

16. The method of claim 11, wherein each of the plurality of temperature readings is received within about 48 hours after surgery.

17. The method of claim 11, further comprising:
transmitting an alert regarding the potential for infection to a receiving unit using the communications interface of the electronics component.

18. The method of claim 11, further comprising:
decoupling the electronics component from the temperature sensing layer;
removing the wound dressing comprising the temperature sensing layer from the wound;
applying a subsequent wound dressing to the wound, the subsequent wound dressing comprising a subsequent temperature sensing layer; and
coupling the electronics component to the subsequent temperature sensing layer.

* * * * *